US010610565B2

(12) United States Patent
Feinerman et al.

(10) Patent No.: US 10,610,565 B2
(45) Date of Patent: Apr. 7, 2020

(54) PREVENTION AND TREATMENT OF OCULAR SIDE EFFECTS WITH A CYCLOSPORIN

(71) Applicant: Allergan, Inc., Irvine, CA (US)

(72) Inventors: Gregg Feinerman, Irvine, CA (US); Neil Barth, Laguna Beach, CA (US); Rhett M. Schiffman, Laguna Beach, CA (US); Pamela S. Barnett, Aliso Viejo, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 15/837,776

(22) Filed: Dec. 11, 2017

(65) Prior Publication Data

US 2018/0325996 A1 Nov. 15, 2018

Related U.S. Application Data

(60) Continuation of application No. 13/957,858, filed on Aug. 2, 2013, now Pat. No. 9,839,667, which is a continuation-in-part of application No. 12/825,116, filed on Jun. 28, 2010, now Pat. No. 8,501,174, which is a division of application No. 11/548,631, filed on Oct. 11, 2006, now Pat. No. 7,745,400.

(60) Provisional application No. 60/596,709, filed on Oct. 14, 2005, provisional application No. 60/597,431, filed on Nov. 30, 2005, provisional application No. 60/805,577, filed on Jun. 22, 2006.

(51) Int. Cl.
A61K 31/337 (2006.01)
A61K 38/13 (2006.01)
A61K 45/06 (2006.01)
A61K 31/7072 (2006.01)
A61K 36/13 (2006.01)

(52) U.S. Cl.
CPC ............ *A61K 38/13* (2013.01); *A61K 31/337* (2013.01); *A61K 31/7072* (2013.01); *A61K 36/13* (2013.01); *A61K 45/06* (2013.01)

(58) Field of Classification Search
CPC .... A61K 31/337; A61K 38/13; C07D 305/14; C07K 7/645
See application file for complete search history.

(56) References Cited

U.S. PATENT DOCUMENTS

| 4,839,342 | A | 6/1989 | Kaswan |
| 5,294,604 | A | 3/1994 | Nussenblatt et al. |
| 5,411,952 | A | 5/1995 | Kaswan |
| 5,977,067 | A | 11/1999 | Evers et al. |
| 6,245,805 | B1 | 6/2001 | Broder et al. |
| 6,254,860 | B1 | 7/2001 | Garst |
| 6,395,770 | B1 | 5/2002 | Broder et al. |
| 6,787,306 | B1 | 9/2004 | Gonzalez et al. |
| 7,141,576 | B2 | 11/2006 | Lackey et al. |
| 7,745,400 | B2 | 6/2010 | Feinerman |
| 7,772,274 | B1* | 8/2010 | Palepu ................. A61K 9/0019 514/449 |
| 8,501,174 | B2 | 8/2013 | Feinerman et al. |
| 9,839,667 | B2* | 12/2017 | Feinerman ............. A61K 45/06 |
| 2001/0041671 | A1 | 11/2001 | Napoli |
| 2002/0025943 | A1 | 2/2002 | Bradley et al. |
| 2002/0045601 | A1 | 4/2002 | Kawashima et al. |
| 2002/0081338 | A1 | 6/2002 | MacKeen |
| 2003/0083366 | A1 | 5/2003 | Grove et al. |
| 2003/0158249 | A1 | 8/2003 | Chi et al. |
| 2003/0166507 | A1 | 9/2003 | Li et al. |
| 2003/0191179 | A1 | 10/2003 | Joshi-Hangal et al. |
| 2003/0216431 | A1 | 11/2003 | Raut |
| 2003/0225011 | A1 | 12/2003 | David et al. |
| 2004/0076691 | A1 | 4/2004 | Haines et al. |
| 2004/0092435 | A1 | 5/2004 | Peyman |
| 2005/0025810 | A1 | 2/2005 | Peyman |
| 2005/0043258 | A1 | 2/2005 | Bennett et al. |
| 2005/0059583 | A1* | 3/2005 | Acheampong ....... A61K 9/0048 514/20.5 |
| 2005/0085438 | A1 | 4/2005 | Cardozo et al. |
| 2005/0272755 | A1 | 12/2005 | Denis et al. |
| 2005/0272758 | A1 | 12/2005 | Bayever et al. |
| 2005/0282734 | A1 | 12/2005 | Kadima et al. |
| 2006/0018910 | A1 | 1/2006 | Gualberto et al. |
| 2006/0046993 | A1 | 3/2006 | Forino et al. |
| 2006/0160074 | A1 | 7/2006 | Dorn et al. |
| 2006/0183883 | A1 | 8/2006 | Hummel et al. |
| 2006/0253263 | A1 | 11/2006 | Meshkin |
| 2008/0009437 | A1 | 1/2008 | Xia et al. |
| 2008/0305994 | A1 | 12/2008 | Zhang et al. |
| 2010/0021420 | A1 | 1/2010 | Lyons et al. |
| 2010/0166699 | A1 | 7/2010 | Thompson et al. |
| 2011/0159111 | A1 | 6/2011 | Curry et al. |
| 2012/0100133 | A1 | 4/2012 | Fisson et al. |
| 2012/0309683 | A1 | 12/2012 | Coy et al. |
| 2013/0252997 | A1 | 9/2013 | Schiffman |

FOREIGN PATENT DOCUMENTS

WO 2006015075 A1 2/2006
WO 2007047334 A1 4/2007

OTHER PUBLICATIONS

Esmaili et al. Blockage of the Lacrimal Drainage Apparatus as a Side Effect of Docetaxel Therapy. Cancer. Aug. 1, 2003, vol. 98, No. 3, pp. 504-507. (Year: 2003).*

Esmaeli, Bita. Management of Excessive Tearing as a Side Effect of Docetaxel. Clinical Breast Cancer. Feb. 2005, pp. 455-457. (Year: 2005).*

Glassman, Michael L. Use drops, irrigation to treat patients with epiphora. Ocular Surgery News U.S. Edition. Aug. 1, 2005 (4 pages). (Year: 2005).*

(Continued)

Primary Examiner — Jeffrey E. Russel
(74) Attorney, Agent, or Firm — Lorenz Siddiqi

(57) ABSTRACT

Therapeutic methods including administration of cyclosporin to an eye of a mammal in combination with administration of a therapeutically active agent effective for treatment of a cancer to said mammal to treat an ocular condition associated with the use of said therapeutically active agent are disclosed herein.

3 Claims, No Drawings

(56) References Cited

OTHER PUBLICATIONS

Akpek, Esen Karamursel et al, A Randomized Trial of Topical Cyclosporin 0.05% in Topical Steroid-Resistant Atopic Keratoconjunctivitis, Ophthalmology, 2004, 476-482, 111.

Calonge, Margarita, The Treatment of Dry Eye, Survey of Ophthalmology, 2001, S227-S239, vol. 45, Supplement 2, Elsevier Science, Inc.

Donnenfeld, Topical cyclosporine A mitigates dry eye associated with graft-versus-host disease, Ocular Surgery News U.S. Edition, Jan. 25, 2011, 1392-1396, 29(12).

Fraunfelder, Frederick T., et al., The Role of Medications in Causing Dry Eye, Journal of Ophthalmology, Jan. 2012, 197-198, vol. 99, No. 2.

Mikhail, S.E., et al., Safety of capecitabine: A review, Expert Opinion on Drug Safety, Aug. 19, 2010, 831-841, vol. 9, No. 5, Informa UK, Ltd.

P. Lanzetta, et al, Major Ocular Complications After Organ Transplantation, Transplantation Proceedings, 2004, 3046-3048, 36, Elsevier, US.

Park, et al., Abstract LB-172: A randomized phase II study of S-1 versus capecitabine as first-line chemotherapy in the elderly metastatic gastric cancer patients with/without poor performance status: clinical and pharmacogenetic results, Cancer Research, Apr. 15, 2013, Supplement, LB-72, vol. 73, No. 8.

Pijpe, J., et al., Rituximab treatment in patients with primary Sjögren's syndrome: An open-label phase II study, Arthritis and Rheumatism, Sep. 2005, 2740-2750, vol. 52, No. 9, American College of Rheumatology.

Questions and Answers about Taxotere Injection Concentrate, Patient Information Leaflet by Aventis Pharmaceuticals Inc., Rev. May 2004.

RESTASIS Brochure, Allergan, Inc. 2014.

Schmid, et al., Update on Ocular Complications of Systemic Cancer Chemotherapy, Survey of Ophthalmology, Feb. 2006, pp. 19-40, vol. 51, No. 1.

South Coast Gynecologic Oncology, Inc., Most Common Chemotherapy Side Effects, 2012, San Diego, http://scgoi.com/chemotherapy/most-common-chemotherapy-side-effects.

Van Cutsem, E., et al., Capecitabine, an oral fluoropyrimidine carbamate with substantial activity in advanced colorectal cancer: Results of a randomized phase II study, Journal of Clinical Oncology, Mar. 2000, 1337-1345, vol. 18, Issue 6, American Society of Clinical Oncology.

Zapata, L.F., et al., Sjögren keratoconjunctivitis sicca treated with rituximab, Cornea, Aug. 2007, 886-887, vol. 26, Issue 7, Lippincott Williams & Wilkiins.

\* cited by examiner

PREVENTION AND TREATMENT OF OCULAR SIDE EFFECTS WITH A CYCLOSPORIN

CROSS-REFERENCE TO RELATED APPLICATIONS

This application is a continuation of U.S. patent application Ser. No. 13/957,858 filed on Aug. 2, 2013, which is a continuation-in-part of U.S. patent application Ser. No. 12/825,116 filed on Jun. 28, 2010, now U.S. Pat. No. 8,501,174, which is a divisional of U.S. Pat. No. 11/548,631 filed on Oct. 11, 2006, now U.S. Pat. No. 7,745,400, which claims priority to: U.S. Provisional Patent Application No. 60/596,709, filed on Oct. 14, 2005; U.S. Provisional Patent Application No. 60/597,431, filed on Nov. 30, 2005; and U.S. Provisional Patent Application No. 60/805,577, filed on Jun. 22, 2006, all of which are expressly incorporated by reference herein.

DESCRIPTION OF THE INVENTION

Patients undergoing treatment with certain therapeutically active agents can have certain ocular conditions as a result of that treatment. In particular, patients undergoing chemotherapy with a therapeutically active agent effective for treatment of a cancer often have ocular conditions as a result of that treatment.

One embodiment is a method comprising administering a cyclosporin, an analog or derivative thereof, or a combination thereof, to an eye of a mammal in combination with administration of a therapeutically active agent to said mammal, said therapeutically active agent being an chemotherapy agent or an antiviral agent, wherein said method is effective in preventing or treating an ocular condition associated with the use of said therapeutically active agent.

"Administration of a therapeutically active agent to said mammal" means administration of the therapeutically active agent to the mammal in any way that a therapeutically active agent may be administered. Thus, administration of the therapeutically active agent is not limited to the eye, but may include systemic administration via oral, intravenous, rectal, or other means; or administration locally to any part of the body by injection, implantation, topical administration, or other means.

Administration of the therapeutically active agent need not exactly overlap in time with the administration of the cyclosporin, an analog or derivative thereof, or a combination thereof. For example, the cyclosporin, analog or derivative thereof, or a combination thereof might be administered to a mammal before the mammal receives any of the therapeutically active agent to avoid the onset of the ocular condition. In another example, the cyclosporin, analog or derivative thereof, or a combination thereof, might be administered after the mammal has begun to receive the therapeutically active agent. In another example, the cyclosporin, analog or derivative thereof, or a combination thereof, might be administered after the mammal has ceased receiving the therapeutically active agent. Administration of the cyclosporin, analog or derivative thereof, or a combination thereof might also be simultaneous with the administration of the therapeutically active agent. Thus, any time relationship may exist between the mammal receiving the therapeutically active agent and the cyclosporin, analog or derivative thereof, or a combination thereof, provided that the use of the latter is reasonably related to treatment or prophylaxis of a condition associated with the former.

It may be convenient to provide a single pharmaceutical composition which comprises both (i) the cyclosporin, analog or derivative thereof, or a combination thereof and (ii) the therapeutically active agent when the agents are to be administered simultaneously.

It may be convenient to provide (i) the cyclosporin, analog or derivative thereof, or a combination thereof and (ii) the therapeutically active agent in form of a kit. For example, the agents may be packaged together. For example, (i) the cyclosporin, analog or derivative thereof, or a combination thereof and (ii) the therapeutically active agent may each be packaged in conventional pharmaceutical packaging such as boxes, jars, blister packs, vials, bottles, syringes etc., and the individually packaged components may then be combined to form a kit e.g. by the use of further packaging such as a box, or by joining up the individual packages. When in kit form, the agents can be taken independently of one another, thus allowing the user freedom to decide the temporal relationship between his use of each of the agents.

Use of a cyclosporin, or an analog or derivative thereof, including cyclosporin A, for the treatment of ocular conditions occurring in a person undergoing treatment with a therapeutically active agent for the treatment of cancer is contemplated. Accordingly, a particular patient group which may benefit from the present invention is that of persons having ocular conditions resulting from the use of a chemotherapy agent.

Also contemplated is use of a cyclosporin, or an analog or derivative thereof, including cyclosporin A, for the treatment of ocular conditions occurring in a person who is undergoing treatment with an antiviral agent. Accordingly, a particular patient group which may benefit from the present invention is that of persons having ocular conditions resulting from the use of an antiviral agent.

Also contemplated is use of a cyclosporin, or an analog or derivative thereof, including cyclosporin A, for the treatment of ocular conditions occurring in a person who is undergoing treatment with an immunomodulator. Accordingly, a particular patient group which may benefit from the present invention is that of persons having ocular conditions resulting from the use of an immunomodulator.

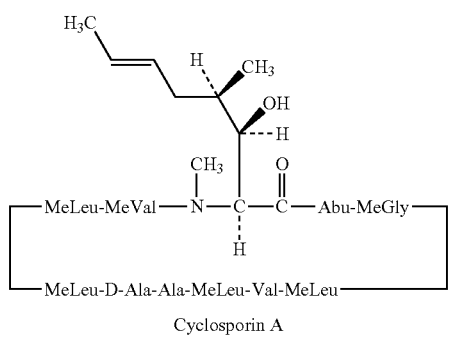

Cyclosporin A

Cyclosporin A is a cyclic peptide with immunosuppressive properties having the structure shown above. It is also known by other names including cyclosporine, cyclosporine A, cyclosporin, and cyclosporin A.

Other cyclosporins include cyclosporine b, cyclosporine D, cyclosporine G, which are well known in the art.

Cyclosporin derivatives and analogs are also known in the art. For example, U.S. Pat. Nos. 6,254,860 and 6,350,442, incorporated by reference herein, illustrate several examples.

The ocular conditions to be prevented or treated are well known in the art. In particular, nasolacrimal stenosis, chemotherapy induced ocular toxicity, lacrimal duct stenosis, punctal stenosis, lacrimation, abnormal lacrimation, (such as tear production that is presumed to be suppressed due to ocular inflammation associated with keratoconjunctivitis sicca), increased tearing, nasolacrimal blockage, keratitis, keratoconjunctivitis, conjunctivitis, or a combination thereof may be prevented or treated. Hence, for example, in one embodiment one administers cyclosporin A to a mammal, in combination with administration of a therapeutically active agent to said, to increase tear production that is presumed to be suppressed due to ocular inflammation associated with keratoconjunctivitis sicca to the mammal, wherein "administration of a therapeutically active agent to said mammal" is as defined above; that is, the cyclosporin A may be administered to the mammal before the mammal receives any of the therapeutically active agent, after the mammal begins to receive the therapeutically active agent, or after the mammal ceases receiving the therapeutically active agent.

Also contemplated is a method comprising administering cyclosporin A topically to the eye of a person, wherein docetaxel is also administered to said person, wherein said method is effective in preventing or treating an ocular condition associated with the administration of docetaxel.

Although the ocular condition may be associated with any antiviral agent, the following
antiviral agents are contemplated in particular:
Zalcitabine, and
Rimantadine Hydrochloride.

Although the ocular condition may be associated with any chemotherapy agent, the following
chemotherapy agents are contemplated in particular:
Paclitaxel and derivatives thereof, such as Docetaxel
Doxorubicin Hydrochloride,
Irinotecan Hydrochloride,
Fluorouracil,
Imatinib Mesylate, and
Rituximab.

Derivatives of paclitaxel generally include the macrocycle shown below, where derivatives are formed at a hydroxyl moiety.

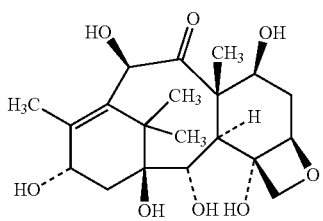

Chemotherapeutic compounds incorporating this structure are thus contemplated. For example, the structures of paclitaxel and docetaxel are shown below.

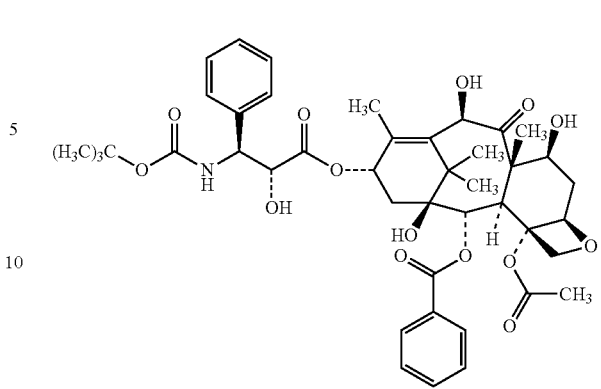

Docetaxel

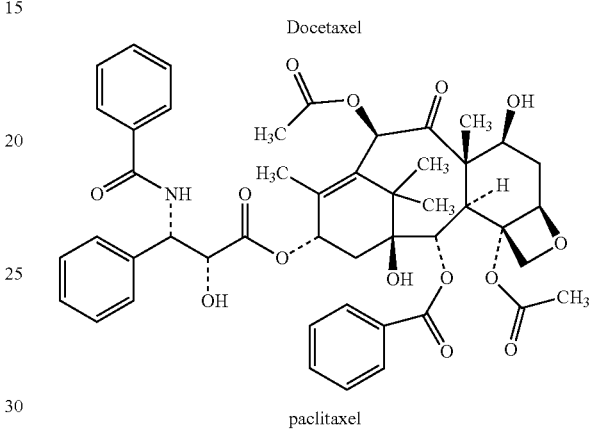

paclitaxel

In one embodiment, the chemotherapy agent is docetaxel.

Although the ocular condition may be associated with any immunomodulator, the following
immunomodulators are contemplated in particular:
Interferon alfa-2b, Recombinant
Mycophenolate Mofetil, and
Mycophenolate Mofetil Hydrochloride.

While not intending to limit the scope of the invention in any way, the following therapeutically active agents may cause lacrimal duct stenosis: docetaxel.

While not intending to limit the scope of the invention in any way, the following therapeutically active agents may cause lacrimation:
interferon alfa-2b, recombinant,
doxorubicin hydrochloride,
irinotecan hydrochloride,
fluorouracil,
docetaxel, and
zalcitabine.

While not intending to limit the scope of the invention in any way, the following therapeutically active agents may cause abnormal lacrimation:
mycophenolate mofetil,
mycophenolate mofetil hydrochloride,
imatinib mesylate,
rituximab, and
rimantadine hydrochloride.

While not intending to limit the scope of the invention in any way, the following therapeutically active agents may cause keratitis:
Amantadine Hydrochloride,
Erlotinib,
Bexarotene, and
Voriconazole.

While not intending to limit the scope of the invention in any way, the following therapeutically active agents may cause keratoconjunctivitis:
Capecitabine.

While not intending to limit the scope of the invention in any way, the following therapeutically active agents may cause conjunctivitis:
Risedronate Sodium,
Leflunomide,
Mycophenolate Mofetil,
Oxaliplatin,
Cetuximab,
Ribavirin,
Rituximab,
Basiliximab,
Erlotinib,
Capecitabine,
Doxorubicin Hydrochloride,
Imiquimod,
Amphotericin B, liposomal,
Zolpidem Tartrate,
Glatiramer Acetate,
Epirubicin Hydrochloride,
Saquinavir,
Enfuvirtide,
Imatinib Mesylate,
Gefitinib,
Lamotrigine,
Delavirdine Mesylate,
Rituximab,
Ivermectin,
Palivizumab,
Oseltamivir Phosphate,
Bexarotene,
Docetaxel,
Abacavir Sulfate,
Lamivudine,
Zidovudine,
Voriconazole,
Nevirapine,
Ribavirin, and
Abacavir Sulfate.

Additionally, one or more of the ocular conditions disclosed herein may be associated with the following therapeutically active agents: abacavir sulfate, amantadine hydrochloride, amphotericin B, basiliximab, bexarotene, capecitabine, cetuximab, delavirdine mesylate, docetaxel, doxorubicin hydrochloride, enfuvirtide, epirubicin hydrochloride, erlotinib, fluorouracil, gefitinib, glatiramer acetate, imatinib mesylate, imiquimod, interferon alfa-2b, irinotecan hydrochloride, ivermectin, lamivudine, lamotrigine, leflunomide, mycophenolate mofetil, mycophenolate mofetil hydrochloride, nevirapine, oseltamivir phosphate, oxaliplatin, palivizumab, ribavirin, rimantadine hydrochloride, risedronate sodium, rituximab, saquinavir, voriconazole, zalcitabine, zidovudine, and zolpidem tartrate.

The therapeutically active agent is administered in the usual manner known in the art for the condition being treated.

Alternatively, a therapeutically active agent and cyclosporin A may be administered in a single composition.

Useful compositions are disclosed in the following patent applications, each of which is expressly incorporated by reference herein: U.S. patent application Ser. No. 11/181,409, filed on Jul. 13, 2005; U.S. patent application Ser. No. 11/181,509, filed on Jul. 13, 2005; U.S. patent application Ser. No. 11/181,187, filed on Jul. 13, 2005; U.S. patent application Ser. No. 11/181,178, filed on Jul. 13, 2005; U.S. patent application Ser. No. 11/181,428, filed on Jul. 13, 2005; U.S. patent application Ser. No. 11/255,821, filed on Oct. 19, 2005; U.S. patent application Ser. No. 11/161,218, filed on Jul. 27, 2005; and U.S. Provisional Patent Application Ser. No. 60/727,684, filed on Oct. 17, 2005.

In one embodiment, cyclosporin A is administered in the form of Restasis®, available from Allergan, Inc. The cyclosporin A is administered twice a day as indicated on the package insert.

Although there has been hereinabove described pharmaceutical compositions for the purpose of illustrating the manner in which the invention may be used to advantage, it should be appreciated that the invention is not limited thereto. Accordingly, any and all modifications, variations, or equivalent arrangements, which may occur to those skilled in the art, should be considered to be within the scope of the present invention as defined in the appended claims.

What is claimed is:

1. A method comprising:
   administering a composition comprising cyclosporin A to a mammal before the mammal receives a therapeutically active agent,
   wherein the therapeutically active agent comprises docetaxel, and
   then administering the therapeutically active agent comprising docetaxel to the mammal in need thereof,
   wherein the method is effective in treating lacrimal duct stenosis in a mammal whose lacrimal duct stenosis is associated with the administration of the therapeutically active agent comprising docetaxel.

2. The method of claim 1, wherein the composition comprises cyclosporin A at a concentration of about 0.05%.

3. The method of claim 2, wherein the composition further comprises castor oil, polysorbate 80, and high molecular weight co-polymers of acrylic acid and a long chain alkyl methacrylate cross-linked with allyl ethers of pentaerythritol.

* * * * *